US006265092B1

United States Patent
Meltser et al.

(10) Patent No.: US 6,265,092 B1
(45) Date of Patent: Jul. 24, 2001

(54) METHOD OF CONTROLLING INJECTION OF OXYGEN INTO HYDROGEN-RICH FUEL CELL FEED STREAM

(75) Inventors: Mark Alexander Meltser; Stanley Gutowski, both of Pittsford, NY (US); Kirk Weisbrod, Los Alamos, NM (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 09/550,054

(22) Filed: Apr. 14, 2000

Related U.S. Application Data (62) Division of application No. 08/957,562, filed on Oct. 24, 1997, now Pat. No. 6,063,576.

(51) Int. Cl.[7] .................................................. H01M 8/04
(52) U.S. Cl. ............................. 429/12; 429/13; 429/17; 429/22; 429/23; 429/90; 204/406
(58) Field of Search ............................... 429/13, 22, 23, 429/12, 17, 90; 204/406; 205/784.5, 784, 783.5, 782

(56) References Cited

U.S. PATENT DOCUMENTS

| | | | |
|---|---|---|---|
| 4,910,099 | * 3/1990 | Gottesfeld | 429/13 |
| 5,601,936 | 2/1997 | Dudfield et al. | 429/13 |
| 5,712,052 | 1/1998 | Kawatsu | 429/13 |
| 5,843,195 | * 12/1998 | Aoyama | 48/127.7 |

FOREIGN PATENT DOCUMENTS

| | | |
|---|---|---|
| 6-251786 | 9/1994 | (JP) . |
| 6-260197 | 9/1994 | (JP) . |

* cited by examiner

*Primary Examiner*—Carol Chaney
*Assistant Examiner*—Angela J. Martin
(74) *Attorney, Agent, or Firm*—Lawrence B. Plant (57) ABSTRACT

A method of operating a $H_2$—$O_2$ fuel cell fueled by hydrogen-rich fuel stream containing CO. The CO content is reduced to acceptable levels by injecting oxygen into the fuel gas stream. The amount of oxygen injected is controlled in relation to the CO content of the fuel gas, by a control strategy that involves (a) determining the CO content of the fuel stream at a first injection rate, (b) increasing the $O_2$ injection rate, (c) determining the CO content of the stream at the higher injection rate, (d) further increasing the $O_2$ injection rate if the second measured CO content is lower than the first measured CO content or reducing the $O_2$ injection rate if the second measured CO content is greater than the first measured CO content, and (e) repeating steps a–d as needed to optimize CO consumption and minimize $H_2$ consumption.

1 Claim, 3 Drawing Sheets

METHOD OF CONTROLLING INJECTION OF OXYGEN INTO HYDROGEN-RICH FUEL CELL FEED STREAM

This is a division of application Ser. No. 08/957,562 filed Oct. 24, 1997 now U.S. Pat. No. 6,063,576.

The Government of the United States of America has rights in this invention pursuant to Agreement No. DE-AC02-90CH10435 awarded by the U.S. Department of Energy.

TECHNICAL FIELD

The present invention relates to a carbon monoxide (CO) sensor, and a method for monitoring the CO concentration in the reformate fuel stream to a PEM fuel cell for controlling such concentration.

BACKGROUND OF THE INVENTION

Fuel cells have been proposed as a power source for many applications. So-called PEM (proton exchange membrane) fuel cells [a.k.a. SPE (solid polymer electrolyte) fuel cells] potentially have high energy and low weight, and accordingly are desirable for mobile applications (e.g., electric vehicles). PEM fuel cells are well known in the art, and include a "membrane electrode assembly" (a.k.a. MEA) comprising a thin, proton transmissive, solid polymer membrane-electrolyte having an anode on one of its faces and a cathode on the opposite face. The membrane-electrode-assembly is sandwiched between a pair of electrically conductive elements which serve as current collectors for the anode and cathode, and contain appropriate channels and/or openings therein for distributing the fuel cell's gaseous reactants over the surfaces of the respective anode and cathode catalysts. The channels/openings for the reactants are often referred to as "flow channels". A plurality of individual cells are commonly bundled together to form a PEM fuel cell stack.

PEM fuel cells are typically $H_2$—$O_2$ fuel cells wherein hydrogen is the anode reactant (i.e., fuel) and oxygen is the cathode reactant (i.e., oxidant). The oxygen can either be in a pure form (i.e., $O_2$), or air (i.e., $O_2$ admixed with $N_2$). The solid polymer membranes are typically made from ion exchange resins such as perfluoronated sulfonic acid. One such resin is NAFION™ sold by E. I. DuPont deNemeors & Co. Such membranes are well known in the art and are described in U.S. Pat. Nos. 5,272,017 and 3,134,697, and in Journal of Power Sources, Volume 29 (1990), pages 367–387, inter alia. The anode and cathode themselves typically comprise finely divided carbon particles, very finely divided catalytic particles supported on the internal and external surfaces of the carbon particles and proton conductive resin intermingled with the catalytic and carbon particles. One such membrane electrode assembly and fuel cell is described in U.S. Pat. No. 5,272,017 issued Dec. 21, 1993 and assigned to the assignee of the present invention.

The hydrogen used in the fuel cell can be derived from the reformation of methanol or other organics (e.g., hydrocarbons). Unfortunately, the reformate exiting the reformer contains undesirably high concentrations of carbon monoxide which can quickly poison the catalyst of the fuel cell's anode, and accordingly must be removed. For example, in the methanol reformation process, methanol and water (as steam) are ideally reacted to generate hydrogen and carbon dioxide according to the reaction:

$$CH_3OH+H_2O \rightarrow CO_2+3\,H_2$$

This reaction is accomplished heterogeneously within a chemical reactor that provides the necessary thermal energy throughout a catalyst mass and actually yields a reformate gas comprising hydrogen, carbon dioxide, carbon monoxide, and water. One such reformer is described in U.S. Pat. No. 4,650,727 to Vanderborgh. Carbon monoxide (i.e., about 1–3 mole %) is contained in the $H_2$-rich reformate/effluent exiting the reformer, and must be removed or reduced to very low nontoxic (i.e., to the anode) concentrations (i.e., less than about 20 ppm) to avoid poisoning of the anode by adsorption onto the anode catalyst. The unreacted water serves to humidify the fuel gas and prevent drying of the MEA.

It is known that the carbon monoxide, CO, level of the reformate/effluent exiting a methanol reformer can be reduced by utilizing a so-called "shift" reaction. In the shift reactor, water (i.e. steam) is injected into the methanol reformate/effluent exiting the reformer, in the presence of a suitable catalyst, to lower its temperature, and increase the steam to carbon ratio therein. The higher steam to carbon ratio serves to lower the carbon monoxide content of the reformate according to the following ideal shift reaction:

$$CO+H_2O \rightarrow CO_2+H_2$$

Some CO survives the shift reaction and remains in the reformate. Depending upon the reformate flow rate and the steam injection rate, the carbon monoxide content of the gas exiting the shift reactor can be as low as 0.5 mole %. Any residual methanol is converted to carbon dioxide and hydrogen in the shift reactor. Hence, shift reactor effluent comprises hydrogen, carbon dioxide, water and some carbon monoxide.

The shift reaction is not enough to reduce the CO content of the reformate enough (i.e., to below about 20 ppm). Therefore, it is necessary to further remove carbon monoxide from the hydrogen-rich reformate stream exiting the shift reactor, and prior to supplying it the fuel cell. It is known to further reduce the CO content of $H_2$-rich reformate exiting the shift reactor by a so-called "PROX" (i.e., preferential oxidation) reaction effected in a suitable PROX reactor and can be either (1) adiabatic (i.e. where the temperature of the catalyst is allowed to rise during oxidation of the CO), or (2) isothermal (i.e. where the temperature of the catalyst is maintained substantially constant during oxidation of the CO). The PROX reactor comprises a catalyst bed operated at temperatures which promote the preferential oxidation of the CO by injecting controlled amounts of air into the effluent from the shift reactor to consume the CO without consuming/oxidizing substantial quantities of the $H_2$. The PROX reaction is as follows:

$$CO+\tfrac{1}{2}\,O_2 \rightarrow CO_2$$

Desirably, the $O_2$ required for the PROX reaction will be about two times the stoichiometric amount required to react the CO in the reformate. If the amount of $O_2$ is substantially less than about two times the stoichiometric amount needed, insufficient CO oxidation will occur. On the other hand, if the amount of $O_2$ exceeds about two times the stoichiometric amount needed, excessive consumption of $H_2$ results. Consumption of the $H_2$ raises the temperature of the gas, which in turn causes the formation of CO by the reaction of $H_2$ with $CO_2$, known as the reverse gas-shift reaction. Hence, careful control of the amount of air injected in the PROX reaction is essential to control the CO content of the reformate feed stream to the fuel cell. The PROX process is described in a paper entitled "Methanol Fuel Processing for Low Temperature Fuel Cells" published in the Program and Abstracts of the 1988 Fuel Cell Seminar, Oct. 23–26, 1988, Long Beach, Calif., and in Vanderborgh et al U.S. Pat. No. 5,271,916, inter alia.

Whether an adiabatic or isothermal PROX reaction, a controlled amount of $O_2$ (i.e., as air), is mixed with the reformate exiting the shift reactor, and the mixture passed through a suitable PROX catalyst bed known to those skilled in the art. To control the air input rate, the CO concentration in the gas exiting either the shift reactor or the PROX reactor is measured, and based thereon, the $O_2$ concentration needed for the PROX reaction adjusted. However, sensitive, real time, CO sensors have not heretofore been available, and accordingly system response to CO concentration variations has been slow. This is particularly troublesome in dynamic systems where the flow rate, and CO content, of the $H_2$-rich reformate vary continuously in response to variations in the power demands on the fuel cell system. Since the amount of $O_2$ (e.g., air) supplied to the PROX reactor must vary on a real time basis in order to accommodate the varying power demands on the system, there is a need for a rapid response CO sensor to continuously monitor the CO in the reformate stream and therefrom (1) maintain the proper oxygen-to-carbon monoxide concentration ratio in the PROX reactor, and/or (2) divert the reformate stream away from the fuel cell until the CO content thereof falls within acceptable levels.

SUMMARY OF THE INVENTION

The present invention provides a sensitive CO sensor utilizing a mini PEM fuel cell as a probe, and a method for real time monitoring of the CO concentration in the reformate feed stream to a PEM fuel cell as a means to control the operation of the fuel cell system. In accordance with the present invention, the sensor is repeatedly refreshed by purging any CO therefrom to maintain the CO sensitivity of the sensor. CO purging may be effected chemically or electrochemically as described hereinafter. The invention is useful during system start-up to determine when the CO level of the PROX effluent is sufficiently low that such effluent can be directed to the fuel cell without poisoning the anode catalyst. The invention is particularly useful for the real-time control of the amount of $O_2$ (i.e., as air) supplied to the PROX reaction in response to the CO concentration in the $H_2$ gas stream exiting the PROX reactor so as to maximize CO consumption while minimizing $H_2$ consumption in the PROX reactor. The CO concentration in the reformate may be measured at various locations in the reformate fuel stream to a fuel cell (e.g., after the reformer, shift or PROX reactions).

In accordance with a preferred embodiment of the present invention, there is provided a CO sensor comprising a PEM-probe, and a method of using the PEM-probe to maintain its sensitivity and provide real time control of the CO content of the reformate fuel stream to a PEM, $H_2$—$O_2$ fuel cell stack. The PEM-probe is essentially a mini PEM fuel cell which, like the stack's cells, has an anode and cathode affixed to opposite sides of a proton exchange membrane and a hydrogen flow channel confronting the anode that receives hydrogen from the hydrogen-feed manifolds supplying the stack. The PEM-probe's anode will preferably have a smaller area and a lower catalyst loading (i.e., $g/cm^2$) than the stack's cells for increased CO sensitivity compared to that of the stack itself. Most preferably, the surface area of the PEM-probe's electrodes will be less than about 10% that of the stack's electrodes, and the catalyst loading will be about half the catalyst loading in the stack's cells. Moreover, in accordance with the present invention, sensitivity of the PEM-probe is enhanced even further by intermittently purging the probe's anode catalyst of any CO that might have become adsorbed thereon while monitoring the reformate gas fed to the fuel cell. The frequency of purging is such as to maintain the catalyst in a substantially CO-free, or near CO-free, condition where the probe is most effective and responsive in detecting CO buildup on its catalyst over short intervals. In this regard, the probe is quite effective/responsive during the early stages of contamination, but less so as the probe becomes more and more contaminated with CO. CO purging will preferably be effected by raising the anode potential sufficiently [(i.e., to at least 0.8 V measured against a reversible hydrogen electrode (RHE)] to electrochemically oxidize any CO on the catalyst to $CO_2$ by reaction with the water present in the fuel stream. This may be accomplished by reverse biasing or short circuiting the PEM-probe, as described hereinafter. Alternatively, the probe may be flushed with $O_2$ (e.g., air) to chemically oxidize the CO.

The preferred CO sensor includes means for effecting the intermittent electrochemical purging of the PEM-probe to remove adsorbed CO. In one embodiment, the CO sensor comprises: a gas-monitoring PEM-probe including a proton exchange membrane having an anode and a cathode affixed to opposing first and second surfaces of said membrane; a first electrical current collector engaging the anode; a second electrical current collector engaging the cathode; an electrical discharge circuit connectable between the current collectors, wherein the discharge circuit has a first electrical resistance valued for discharging the PEM-probe at a first rate selected to monitor the degrading output of the PEM-probe incident to CO contamination of the anode; an electrical purging circuit connectable between the current collectors, wherein the purging circuit has a second electrical resistance which is less than the first electrical resistance such that upon discharge of the PEM-probe through the second resistance the potential of the anode is raised to at least 0.8 V (RHE) to effect electrochemical oxidation of any CO adsorbed on the anode; and an electrical switch in electrical series connection between the current collectors and adapted to intermittently, alternately electrically connect the current collectors to the discharge and the purging circuits. In this embodiment, the sensor will also preferably include a motorized valve for shutting off $H_2$ flow to the PEM-probe during the purging stage. Most preferably, the switch for switching between the discharge and the purging circuits will be built into the $H_2$ shut-off valve for simultaneous stopping of the $H_2$ flow to the probe and connecting it to the purging circuit during the purging cycle and vice versa during the discharge cycle.

In another, and most preferred embodiment, a CO sensor is provided that comprises: a gas-monitoring PEM-probe including a proton exchange membrane having an anode and a cathode affixed to opposing first and second surfaces of said membrane; a first electrical current collector engaging the anode; a second electrical current collector engaging the cathode; an electrical discharge circuit connectable between the current collectors; the discharge circuit having a first electrical resistance valued for discharging the PEM-probe at a rate selected to monitor the degrading output of the PEM-probe incident to CO contamination of the anode; an electrical purging circuit connectable between the current collectors and including a voltage source that imposes a reverse electrical bias on the PEM-probe sufficient to raise the potential of the anode to at least about 0.8 V (RHE) to effect electrochemical oxidation of any CO adsorbed on the anode; and an electrical switch in electrical series connection between the current collectors and adapted to intermittently, alternately connect the contacts to the discharge and purging circuits. This embodiment is seen to permit the quickest and most controllable purging of the anode, without the need to shut off the $H_2$ flow.

In accordance with the process of the present invention, the PEM-probe is intermittently purged of any CO buildup on its catalyst. Between such purgings, the current and/or voltage outputs of the probe is/are monitored and compared to reference standards to determine the CO concentration in the reformate (e.g., PROX effluent). More specifically, the process invention contemplates:

a. providing a CO sensor including a monitoring PEM-probe comprising a proton exchange membrane having an anode and a cathode affixed to opposing first and second surfaces of the membrane wherein the anode comprises a catalyst which is susceptible to poisoning incident to the adsorption of CO by the catalyst and consequent progressive degradation of the catalyst from a peak performance level in the early stages of CO adsorption to a poor performance level at later stages of such adsorption;
 b. contacting the anode with a portion of the $H_2$ feed stream to the fuel cell over a plurality of predetermined time intervals;
 c. contacting the cathode with oxygen;
 d. discharging the PEM-probe during the time intervals;
 e. monitoring the electrical output from the PEM-probe during the discharging to generate an output signal having a behavioral pattern indicative of variations in the CO concentration in the feed stream;
 f. from a reference PEM-probe similar to the monitoring PEM-probe, determining a plurality of telltale electrical outputs which are correlated to known CO concentrations in the feed stream;
 g. storing the telltale electrical outputs in a readable memory;
 h. comparing the output signal from the monitoring sensor to the telltale electrical outputs from the reference PEM-probe to identify a telltale electrical output that is substantially similar to the behavioral pattern to determine the CO concentration in the feed stream; and
 i. periodically, purging the catalyst of the CO between the time intervals to maintain the catalyst at substantially its peak performance level.

Once the CO concentration has been determined, a determination can be made as to what adjustments to the system are required. Hence for example, in one scenario, the $O_2$ injection rate to the PROX reactor may be varied, or in another scenario, the PROX effluent may be directed away from the fuel cell stack until its CO content falls within acceptable limits (i.e. below ca. 20 PPM)

BRIEF DESCRIPTION OF THE DRAWINGS

The invention will be better understood when considered in the light of the following detailed description thereof which is given hereafter in conjunction with the following drawings of which.

DESCRIPTION OF THE PREFERRED EMBODIMENT

Briefly, the sensor of the present invention preferably monitors the current through, and voltage across, a constant load connected to the PEM-probe which is connected to hydrogen fuel feed manifold to the fuel cell stack for testing the gas therein. A voltage sensing device senses any voltage fluctuations across the constant load over a predetermined time interval and outputs a voltage signal which represents the behavior pattern of the voltage fluctuations over that interval. A current sensing device senses any current fluctuations through the constant load over a predetermined time interval and outputs a signal which represents the behavior pattern of the current fluctuations over that interval. A first data processing device serves as a data acquisition unit, and, using conventional technology, samples the current and voltage signals, conditions the signals to filter out signal noise, and converts them to digital data streams. A suitable memory device stores telltale voltage and current outputs which have been correlated to known CO concentrations at various temperatures and pressures in a gas like that of the reformate. In this regard, the telltale outputs will have been previously generated empirically from a reference cell which is similar to the PEM-probe and has been discharged in a manner similar to the PEM-probe (e.g., has the same resistance thereacross as the load connected to the PEM-probe). The reference cell is operated over a wide range of known CO-concentrations in the $H_2$ feed stream to develop a library of telltale current and/or voltage outputs corresponding to different CO-concentrations. Finally, a second data processing device (e.g., a personal computer) receives the digital data streams, plots a curve of the behavior pattern of the voltage and current fluctuations from the PEM-probe over a given time interval, and compares those voltage and current behavior patterns to the telltale voltage and current outputs determined from the reference cell in order to match, or otherwise identify, at least one of the telltale outputs that is substantially similar to the behavior pattern being compared. Preferably, the comparison methodology and telltale outputs are those described in copending U.S. patent application U.S. Ser. No. 08/807,559 filed Feb. 28, 1997 in the name of M. Meltzer, and assigned to the assignee of this invention, which is intended to be herein incorporated by reference. Alternatively, rather than plotting the entire behavior pattern and telltale outputs, an abbreviated relationship between the behavior patterns and the telltale outputs can be used. For example, the starting and ending voltages are determined for the beginning and end of a predetermined increment of time and the voltage changes over that increment assumed to vary linearly with time. The reference cell's telltale voltages corresponding to known CO-concentrations in the $H_2$ stream are determined in the same manner. The slopes of the two curves are then compared. In either event, a substantial match between the PEM-probe's output pattern and a telltale output from the reference cell indicates the real time CO-concentration in the hydrogen-feed stream which is then used to trigger adjustments to the reformer, shift and/or PROX reactions to reduce the CO content of the $H_2$ feed stream to the fuel cell stack, or to divert the reformate stream away from the fuel cell stack, if necessary.

Figure 1:
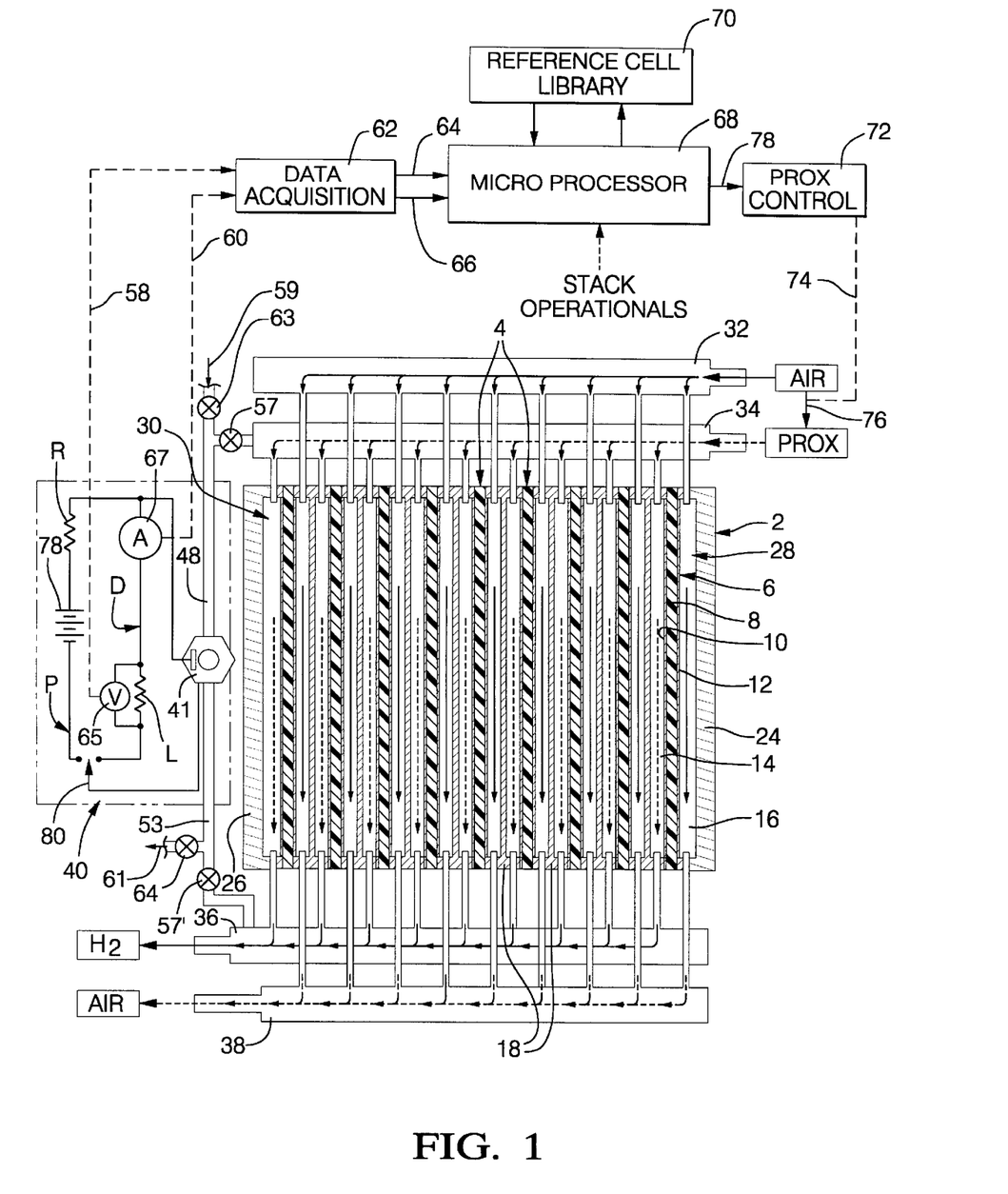
FIG. 1 is a schematic illustration of a bipolar, PEM fuel cell stack, and a preferred CO sensor therefor in accordance with the present invention.

More specifically, FIG. 1 depicts a stack 2 of individual fuel cells 4 each comprising a MEA 6 having a proton conductive resin membrane 8 sandwiched between an anode 10 on one surface thereof and a cathode 12 on the opposite surface thereof. A cathode flow channel 16 is provided adjacent the cathode 12 for flowing an oxygen-rich gas (i.e., preferably air) by, and into contact with, the cathode 12. Similarly, an anode flow channel 14 is provided adjacent the anode 10 for flowing hydrogen fuel by, and into contact with, the anode 10. The membrane 8 will preferably comprise a perfluoronated sulfonic acid polymer such as NAFION™ as is well known in the PEM fuel cell art. Each individual cell 4 is separated from the next cell 4 in the stack by a bipolar plate 18, which is a conductive plate (e.g., metal, carbon, etc.) which separates the several cells one from the next while conducting electrical current in electrical series directly from one cell to the next. End plates 24 and 26 terminate the stack 2 and define the respective cathode and anode flow channels for the end cells 28 and 30 of the stack 2. An oxygen-feed manifold 32 supplies air to the several cathode flow channels 16. Similarly, an hydrogen-feed manifold 34 supplies hydrogen fuel to the several anode flow channels 14. An hydrogen exhaust manifold 36 collects anode exhaust gas from the several anode flow channels 14 for discharge from the stack. Similarly, a cathode exhaust gas manifold 38 collects exhaust gas from the cathode flow channels 16.

Stack performance degrades due to carbon monoxide poisoning of the anode catalyst. Such poisoning is a potential problem when there is excess (i.e., more than about 20 PPM) CO in the hydrogen-feed stream which can result from inefficient methanol/hydrocarbon reforming, shift and/or PROX reactions known to artesans skilled in this art. Accordingly, when the presence of excess CO in the $H_2$ fuel stream is evident, efforts must be made to correct the problem, preferably at its source. To this end, the present invention provides a sensitive, rapid response carbon monoxide sensor (CO-sensor) 40, and method of operating same, which senses CO concentration in the reformate fuel stream in the manifold 34. CO-sensor 40 includes a probe 41 (hereinafter PEM-probe) which is naught but a small (i.e., mini) PEM fuel cell similar to the cells 4 in the stack 2, except for size and possibly catalyst loading. While monitoring the fuel stream in manifold 34, the PEM-probe 41 is discharged in such a manner as to output an electrical signal whose behavioral pattern over time is dependent on the CO concentration in the reformate fuel stream. The output signal behavior pattern is compared to certain telltale outputs from a reference PEM probe identical to the gas-monitoring PEM-probe which have been correlated to known concentrations of CO in $H_2$ at various temperatures and pressures. Conventional pattern recognition technology is preferred for reliably comparing the PEM-probe's 41 output(s) to the telltale output(s) of the reference cell. However, less sophisticated telltale outputs (e.g., approximate slope of voltage degradation curve) may also be used. Monitoring the electrical performance of the PEM-probe 41 and comparing it to the expected performance under known CO concentrations conditions provided by the reference PEM probe provides a direct knowledge of the CO concentration in the reformate feed stream to the fuel cells 4 comprising the stack 2. From this knowledge, needed corrections can be made to the reformer, shift or PROX reactions to bring the CO concentration to within acceptable levels. Alternatively, the fuel stream can be diverted away form the fuel cell stack until the CO content thereof is corrected to within acceptable limits. To control the PROX reaction: (1) the CO concentration is measured at a given $O_2$ injection rate to the PROX reactor; (2) the $O_2$ injection rate is increased and the CO concentration again determined; and (3) if the CO concentration goes down, too little $O_2$ is being injected and if it goes up, too much $O_2$ is being injected. The process is repeated at different $O_2$ injection rates until optimization is achieved.

Figures 2, 4:
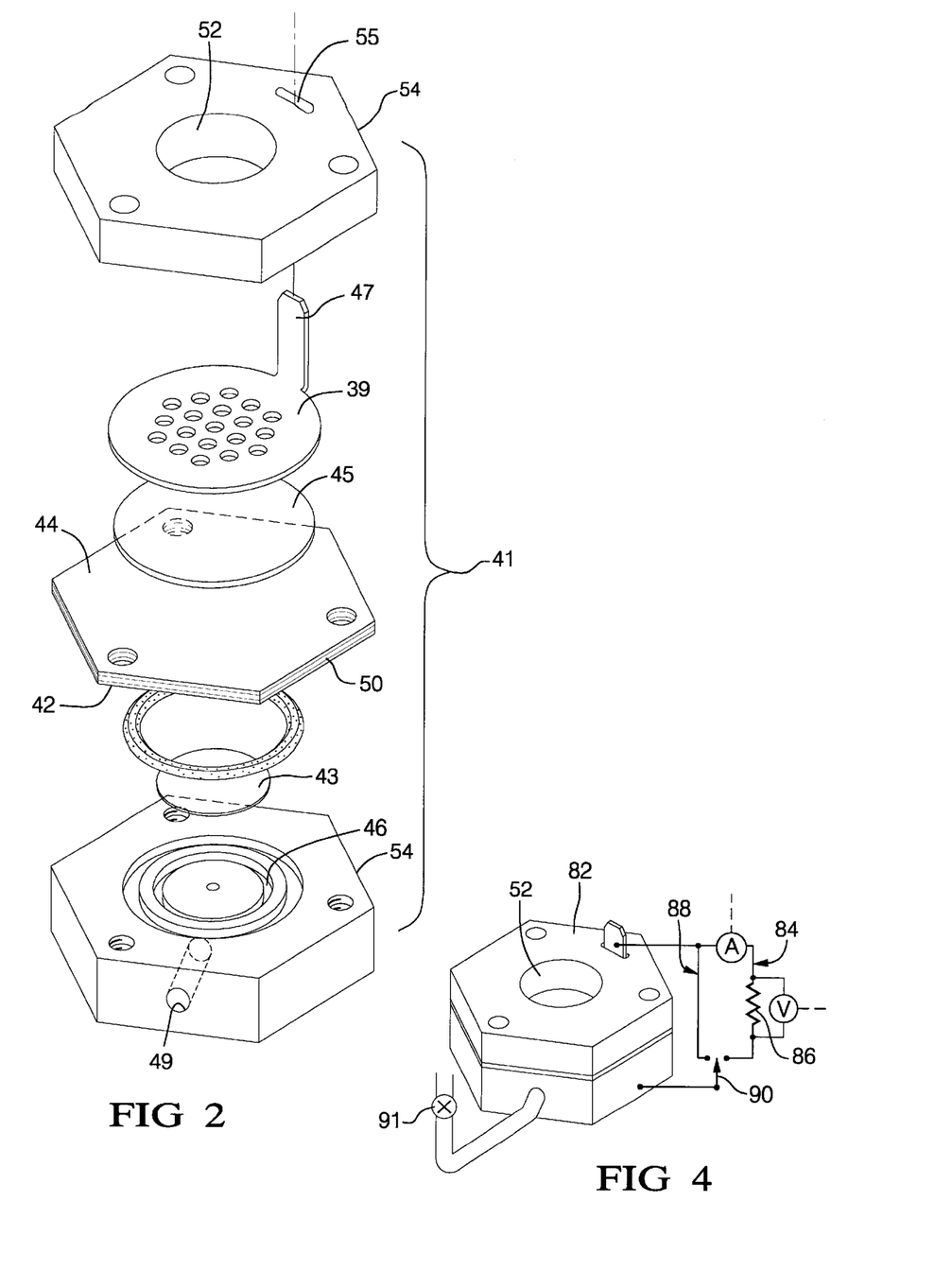
FIG. 2 illustrates an exploded, perspective view of a PEM-probe according to one embodiment of the present invention.
FIG. 4 schematically depicts another embodiment of a CO sensor in accordance with the present invention.
Figure 3:
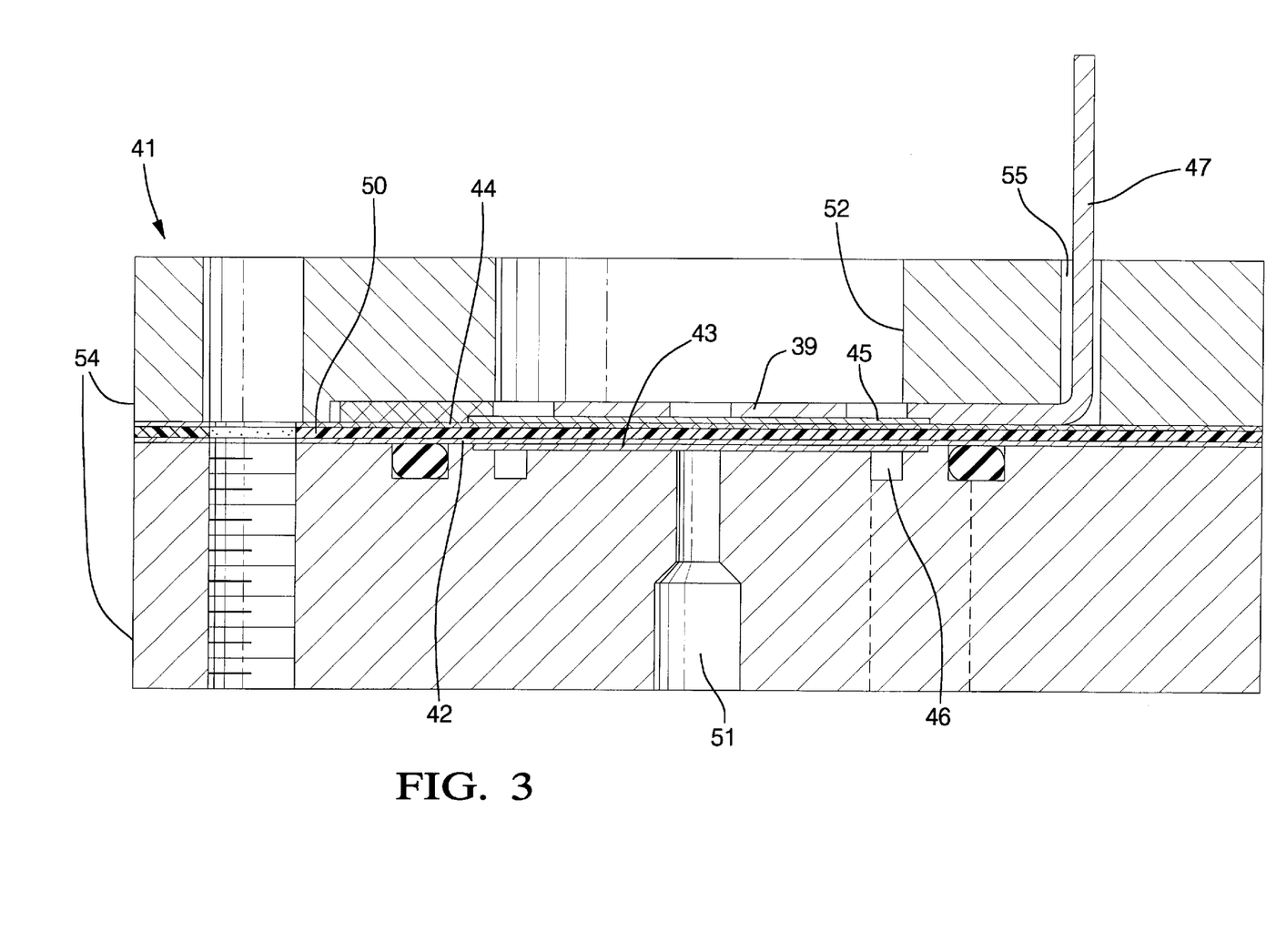
FIG. 3 is a sectioned view of the PEM-probe of FIG. 2.

Like the cells that comprise the stack 2, the PEM-probe 41 includes an anode 42 and cathode 44 on the opposite surfaces of a proton exchange membrane 50 (see FIGS. 2 and 3). Conventional conductive diffusion 43 and 45 contact the anode 42 and cathode 44 respectively. Such material may comprise carbon paper, fine wire mesh, sintered porous metal (e.g., titanium or niobium). The PEM-probe 41 includes an anode flow channel 46 in the housing 54 which communicates with the hydrogen-feed manifold 34 via appropriate flow passages (e.g. inlet 49 and/or conduit 48), as well as the hydrogen exhaust manifold 36 via outlet 51 and conduit 53. The cathode 44 is exposed to ambient air via opening 52 in the PEM-probe's housing 54. Ambient air operation keeps the PEM probe temperature low without external cooling, which increases the CO sensitivity of the PEM-probe. A perforated metal current collector 49 contacts the carbon paper 45 and conducts current to terminal 47 thereof which exits the housing 54 through slot 55. Preferably, the PEM-probe 41 will have a lower catalyst loading than the stack cells 4 to increase its sensitivity to low CO-concentrations. Most preferably, the stack cells 4 will have anodes 10 and cathodes 12 whose surface areas are much greater (e.g., as much as 10 times greater) than the surface areas of the anode 42 and cathode 44 of the PEM-probe 41. This small area, coupled with lower catalyst loadings, provides a PEM-probe with heightened CO-concentration sensitivity. By way of example, an $H_2$—$O_2$ PEM fuel cell stack 2 having individual cells 4 with about 100 $in^2$ of electrode area, can be effectively monitored with a PEM-probe 41 having an electrode area of about 1 $in^2$ to 2 $in^2$, and about one half the catalyst loading (i.e., $g/cm^2$) of the stack cells 4. The conduits 48 and 53 may include valves 57 and 57' for isolating the probe 41 from the $H_2$ manifolds 34 and 36 during purging, if desired. The conduits 48 and 53 may also include air inlet 59 and outlet 61 respectively with associated valves 63 and 64 for controlling the flow of purging air through the PEM-probe 41 (i.e., when the air purging embodiment is used).

Because of its small size and/or low catalyst loading, the anode catalyst of the PEM-probe poisons at a faster rate then the fuel cell stack it is monitoring. Hence, the degradation rate of the electrical outputs of the PEM-probe is greater than that of the stack and provides a more demonstrative indicator of CO concentrations in the $H_2$ fuel stream to the stack. However, the PEM-probe becomes progressively less sensitive to CO concentration variations as it becomes more poisoned. In this regard, the peak performance level of the catalyst is at the point where it has substantially no, or very little, CO adsorbed therein, and the poorest performance when a substantial amount of CO is adsorbed on the catalyst. In accordance with the present invention, sensitivity of the PEM-probe is maintained near its peak performance level by intermittently purging the PEM-probe's anode catalyst of any CO that might be adsorbed therein. Preferably, purging will be accomplished by raising the anode potential to a level sufficient to electrochemically oxidize the CO to $CO_2$ in the presence of water. Typically, this requires raising the anode potential to at least 0.8 V as measured against a reversible hydrogen electrode (RHE), and may be accomplished by (1) periodically short circuiting the PEM-probe as by discharging it through a low resistance load, or (2) most preferably, by periodically reverse biasing the PEM-probe by means of a supplementary voltage source. Alternatively, CO purging may be effected by flushing the anode catalyst with oxygen (e.g. air) to chemically oxidize the CO. The CO sensitivity of the PEM-probe may also be increased by cooling the $H_2$ stream by means of a heat exchange (not shown) inserted in feed line 48 to the PEM-probe 41. Cooling to about 20° C.–90° C. is useful to condense out excess water which impedes sensitivity of the probe.

The most preferred purging technique is to reverse bias the PEM-probe, as this technique is seen to be most easily controlled and performable without shutting off the flow of gas to the PEM-probe. To this end, a CO sensor 40 (see FIG. 1) is provided which includes a PEM-probe 41, a voltage source 78 (e.g. a capacitor, or voltaic device such as a battery or connection to one or more cells 4 of the stack 2) in a purging circuit P, a motorized switch 80, and a discharge circuit D. The switch 80 will preferably be coupled to a timer or clock which periodically switches the PEM-probe between a discharge mode through load L of the discharge circuit D, and a reverse biased mode in the purging circuit P. The purging circuit P also includes a small (e.g., about 0.5 ohm) resistor to avoid a high current surge upon switching between circuits D and P. More specifically, the PEM-probe 41 is coupled to a constant load L in a discharge circuit D (see FIG. 1). A voltage sensing device 65 (e.g., voltmeter) senses the voltage across the load L while a current sensing device 67 (e.g., ammeter) senses the current flowing in the discharge circuit D. The PEM-probe 41 will typically operate with closed circuit voltages of about 0.4–0.9 volts and currents densities of about 0.1 to 1.0 amps/$cm^2$. The voltage sensing device 65 may be any such device as is well known in the art and is capable of outputting a signal 58. The current sensing device 67, on the other hand, may either be (1) a discrete such device as is well known in the art and is capable of outputting a signal 60, or (2) may be the voltage sensing device 65 from which current can automatically be calculated using Ohm's law. The output signals 58 and 60 of voltage sensing device 65 and current sensing device 67 respectively are inputted into a conventional high speed analog-to-digital converter 62 (i.e., data acquisition unit) which conditions the signal to eliminate noise, and generates digital data streams 64 and 66. A preferred such high speed converter useful with pattern recognition technology a SCU-4 data acquisition system sold by Generic Instruments and Systems Corporation (GenIAS™), as it is capable of reading inputted data, and making all needed computations, in real time.

In accordance with another embodiment of the invention, the PEM-probe is deprived of $H_2$ and essentially short circuited or discharged through a relatively low resistance so as to raise the anode potential up to the oxidation potential of the CO (i.e., 0.8 V RHE). To this end, a CO sensor is provided, as shown in FIG. 4, which comprises a PEM-probe 82 like that described above, a normal discharge circuit 84 discharging through load 86, a short-circuiting purging circuit 88, a motorized switch 90 and a motorized valve 91 for cutting off the $H_2$ during purging. The motorized switch 90 and motorized valve 91 will preferably be coupled to a timer or clock which periodically switches the PEM-probe between (1) a normal CO-monitoring discharge mode through load 86 of the discharge circuit 84, and (2) a rapid discharge mode effected by short circuiting the PEM-probe in the purging circuit 88. Most preferably, the $H_2$ cutoff valve 91 and the switch 90 will be integrated into the same structure/device such that $H_2$ cutoff and switching between discharge and purging circuits are effected simultaneously.

When using the reverse biasing embodiment, the anode catalyst will preferably comprise platinum black, and the diffusion layer will preferably comprise a porous metal in order to survive the reverse polarity reaction. For the other embodiments, carbon-supported platinum catalyst and a carbon/graphite diffusion layer may be used.

The current and the voltage of the PEM-probe are preferably both sampled on a regular basis (e.g., every 10 to 100 milliseconds) during a specified discharge interval that can vary from about 100 milliseconds to about 10,000 milliseconds. The resulting signals 58 and 60 are conditioned by the converter 62, and the average voltage and current are plotted over that interval of time. These plots depict the behavior patterns for the voltage and the current outputs over that time interval. These behavior patterns are inputted as data streams 64 and 66 into the data processor 68 where they are compared to predetermined reference current and/or voltage telltale outputs stored in memory 70. Operating conditions of the stack (stack operationals) such as fuel/air stream temperature and pressure (i.e., taken from sensors not shown) are also inputted to the data processor 68 to insure that the proper telltale voltage and/or current are selected from the library 70 for a given voltage/current behavior outputted from the sensor 40. The reference voltage and current telltale outputs are empirically determined before hand at various temperatures and pressures from a reference cell which (1) is similar to the PEM-probe 41, (2) is discharged through a constant load having the same value as the constant load L of the CO-sensor 40, and (3) is operated over a wide range of carbon monoxide concentrations in the $H_2$ feed stream. A large library of such telltale outputs is stored in the memory 70, and is available for the comparison to the voltage and current behavior patterns produced by the PEM-probe 41. The voltage behavior pattern and the current behavior pattern of the PEM-probe 41 are compared to each of the many reference voltage and current telltale outputs on file in the memory 70 until at least one of the reference current and/or voltage signatures closest to the behavior pattern of the PEM-probe's current is identified, and/or one of the reference voltage signatures closest to the behavior pattern of the PEM-probe's voltage is identified. Once a "match" is made between a reference telltale output and a behavior pattern, the CO-concentration in the $H_2$ feed stream is determined from which adjustments can be made, as needed. A perfect match between the behavior patterns and the telltale outputs is not necessary. Rather, a suitable match will be found if the telltale output is substantially similar to the behavior pattern with which it is being compared. By "substantially similar" is meant a degree of similarity that falls within certain pattern recognition tolerances that the stack designer or operator can include in the pattern recognition software to be described hereafter. These tolerances permit a "match" to be made even though the signature and the pattern are not identical.

The data processor 68 includes a common digital computer with associated read-only memory (ROM), read-write random access memory (RAM), electrically programmable read-only memory (EPROM), memory for storing a library of predetermined reference current and voltage signatures for comparing to voltage and current patterns produced by the PEM-probe 41, and input/output sections which interface with the A-D converter 62 and the PROX control 72 that controls the air injection rate to the PROX reactor by means of control signal 74 to a controllable injector 76, or the like. The read-only memory (ROM) of the digital computer contains the instructions necessary to implement the basic input/output instructions. The electrically programmable read-only memory (EPROM) contains the instructions necessary to implement the data processor's own internal control, data manipulation, and communication algorithms. The processor 68 communicates with the A-D converter 62 and the PROX control 72 by means of any appropriate communication network protocol, many of which are known in the art. A standard 486 or Pentium computer with 16 meg of RAM, Running Windows® 3.1 or Windows® 95, and fitted with an ACB 530 bus control board is adequate for this purpose. A specific program for carrying out the functions of the processor 68 may be accomplished by standard skill in the art using conventional information processing languages.

Either the complete voltage and/or current pattern from the PEM-probe 41 may be used, or an abridged pattern (i.e., approximate slope of degradation curve) characterized by (1) a current and/or voltage reading at the beginning of a discharge cycle and (2) a current and/or voltage reading at the end of a discharge cycle may be used. Preferably, the complete pattern will be used, and can be recognized using commercially available pattern recognition programs. Pattern recognition programs are known in the art and have been used for numerous applications such as to (1) identify sea creatures from their acoustic patterns, (2) identify body hormonal changes from sensor measurements, (3) identify the fracture point in a tool using vibration patterns, (4) identify land vehicles from their acoustic and seismic signatures, (5) identify wear patterns in materials from thickness measurements, (6) identify intruders in secure areas using microwave and IR measurements (7) identify automotive intrusion from shock and acoustic patterns, and (8) identify faulty power-seat assemblies from acoustic patterns, inter alia. Preferred pattern recognition software for the CO concentration monitoring technique of the present invention is essentially analog pattern recognition software which, based on current and voltage measurements taken over the specified time intervals, is capable of creating voltage and current behavior patterns that can be compared to reference current and voltage telltale outputs within a defined tolerance range. From such comparisons, the carbon monoxide concentration in the $H_2$ feed stream to the stack can be determined, and based thereon necessary adjustments to the reformer, shift and/or PROX reactions made. A preferred such pattern recognition software is commercially available under the name Failure/Wear Predictor™ (FWP)™ commercially available from the GenIAS™, supra. The FWP™ software has embedded therein GEN-MATCH™ software (also sold by GenIAS™), which is a programmable analog pattern recognition program which can simultaneously measure an arbitrary number of pattern features, and includes three different tolerances for addressing several features of a pattern rather than just a single feature (e.g., a peak) thereof. That software consists of a template-matching process based on a reference signature (i.e., telltale output) created in advance from a reference cell operated under controlled conditions. It is neither amplitude-sensitive nor time-sensitive in that input signals over wide dynamic ranges (e.g., microvolts to volts taking place over periods from nanoseconds to minutes) are normalized to just 600 dimensionless units in amplitude (Y axis) and 2000 dimensionless units in time (X axis). Following normalization of the signals, an accumulated slope, known as "anglesum", is computed for each of the 2000 data points of the normalized input data while traversing the signal contour. Anglesum is proportional to the accumulated slope of the curve in such a way that as the curve increases along a positive slope the anglesum increases in magnitude, and as the curve decreases along a negative slope the anglesum decreases in magnitude. The pattern recognition process utilizes the anglesum values, within defined tolerances, as defined in the reference signatures. In this regard, all reference telltale outputs contain a series of intervals wherein anglesum values and tolerances are used to characterize each interval. These intervals are the discriminating factors used for signal recognition. If the intervals from the reference "match" (i.e., with consideration of all tolerances) like intervals in the behavior patterns from the PEM-probe, a "match" is declared and identification is complete. The program uses two interval types for its recognition process: so-called "key" and "standard" intervals. The key intervals allow phase adjustment of the reference telltale outputs to the behavior patterns from the PEM-probe as well as a first pass discrimination by the recognition process. The standard intervals are then used for the remaining recognition process. Key intervals are selected for uniqueness and serve to minimize search/comparison time through the reference telltale output database as well as to phase align the reference intervals with the data being identified. Hence, key intervals allow the software to quickly ascertain whether the behavior pattern contains the initial characteristics required by the reference signature. If the characteristics of the key intervals are found in the PEM-probe pattern, a full comparison is initiated using the remaining standard intervals. Standard intervals are, by definition, all intervals other than the key intervals. For the PEM-probe's behavior pattern to contain the characteristics of the reference key intervals, it must satisfy two criteria. First, the anglesum values of the reference telltale outputs must match corresponding anglesum values in the PEM-probe's pattern, within the same intervals. Second, the separation (number of data points apart) of the two intervals must be the same as that in the reference telltale outputs. Hence, it is both the intervals and their separation which determine a match.

The reference output template consists of a series of signal intervals to which both X and Y tolerances are assigned. Each telltale output can be divided into as many as 2000 segments each of which is bounded by a signal maximum and minimum. The behavior of the signal between segment boundaries is modeled by a measurement including amplitude change, average rate of amplitude change, and instantaneous rate of amplitude change. Tolerances can be assigned in three areas, for each segment, i.e., so-called "anglesum tolerance", "bit tolerance" and "masking tolerance". Bit tolerance identifies the number of elements (points) beyond the start and end points of the specified reference interval within which the matching process searches for an anglesum match. For example, consider a reference interval with start and end points at data elements 65 and 135, respectively, and a bit tolerance of 5. The matching process will then look at anglesum values in the signal pattern with start and end points of (60, 130), (61, 131), (62, 132), (63, 133), (64, 134), (65, 135), (66, 136), (67, 137), (68, 138), (69, 139), and (70, 140), when trying to match with the reference interval anglesum. If the bit tolerance=0, then the anglesum of the corresponding interval in the data is compared directly to the anglesum of the corresponding interval in the reference pattern. Anglesum tolerance provides an allowance for variation in the anglesum values being compared. This tolerance dictates the allowable error in anglesum values between an interval in a reference telltale output and a corresponding interval in the PEM-probe's data set. Consider a reference interval with start point at 65 and end point at 135 with an anglesum value=100, bit tolerance=0, and anglesum tolerance=5. The intervals will match if the anglesum for the signal data interval starting at 65 and ending at 135 is within the range of 95≦signal anglesum≦105. Masking tolerance stipulates the number of non-matching intervals that can exist and still provide recognition. For example, consider a reference pattern with 30 intervals and a masking tolerance equal to 5. If the number of reference intervals found to match corresponding intervals in the signal data set is ≧25 there is a match. Otherwise, the reference telltale output does not match the PEM-probe's behavior pattern.

During the matching process, the software moves the reference telltale output segment (the template) back and forth along the X-axis within the limits set by the bit tolerance. The software looks for a match with a data segment from the PEM-probe's behavior patterns having an anglesum between the selected upper and lower tolerance limits. Essentially then, the matching process is as follows: (1) a specified width of voltage and/or current data is extracted from the PEM-probe; (2) this data is normalized to an anglesum of 600 points, and an element composition of 2000 points; (3) the reference telltale output template is moved across the data set from the PEM-probe; (4) when a match is found with certain key intervals, the template and PEM-probe data sets are locked in phase, and each data set is jittered in phase along the X-axis looking for the anglesum match; and (5) if the number of data segments specified by the masking tolerance is met, the PEM-probe data set is considered to match the template. When such a match is made, the CO-concentration in the $H_2$ feed stream is determined.

The processor 68 is programmed to perform the comparison process. That is to say, digitized voltage and current values from the data acquisition unit 62 are fed to the processor 68 which calculates the behavior patterns thereof as $I=f(t)$ and/or $V=f(t)$ over a predetermined increment of time. These behavior patterns are then compared to the reference telltale outputs stored in memory 70. If a behavior pattern and a reference telltale output substantially match (as described above), a control signal 78 to the PROX control module 72 is issued to take corrective action (i.e., adjust air injection rate).

While the invention has been disclosed in terms of a specific embodiment thereof it is not intended to be limited thereto, but rather only to the extent set forth hereafter in the claims which follow.

What is claimed is:

1. In a method of operating a $H_2$—$O_2$ fuel cell system comprising the principal steps of (1) providing a hydrogen-rich fuel gas having a first CO content sufficient to poison the fuel cell's anode, and (2) injecting oxygen into said fuel gas upstream of said fuel cell to oxidize said CO with $O_2$ in the presence of said hydrogen to produce a fuel stream for said fuel cell which has a second CO content less than said first content that will not poison said fuel cell, the improvement comprising the sequential steps of:

(a) Determining a first CO concentration in said stream at a first oxygen injection rate;

(b) increasing the oxygen injection rate to a second oxygen injection rate greater than said first oxygen injection rate;

(c) determining a second CO concentration in said stream at said second oxygen rate;

(d) increasing the oxygen injection rate to a third oxygen injection rate greater than said second oxygen rate if said second CO concentration is less than said first CO concentration, or decreasing the oxygen injection rate to a fourth oxygen injection rate less than said third oxygen injection rate if said second CO concentration is greater than said first concentration; and (e) repeating steps a–d above at different oxygen injection rates until an oxygen injection rate is found that optimizes the consumption of CO while minimizing the consumption of $H_2$.

\* \* \* \* \*